United States Patent
Maglione et al.

(10) Patent No.: US 7,364,722 B2
(45) Date of Patent: Apr. 29, 2008

(54) PHARMACEUTICAL AND COSMETIC COMPOSITIONS COMPRISING PLGF-1

(75) Inventors: Domenico Maglione, Anagni (IT); Mauro Battisti, Carpineto (IT); Ettore Conti, Rocca di Papa (IT); Giuseppe Salvia, Cantania (IT); Marina Tucci, Anagni (IT)

(73) Assignee: Geymonat S.p.A., Anagni (IT)

( * ) Notice: Subject to any disclaimer, the term of this patent is extended or adjusted under 35 U.S.C. 154(b) by 9 days.

(21) Appl. No.: 10/507,272

(22) PCT Filed: Mar. 5, 2003

(86) PCT No.: PCT/IT03/00132

§ 371 (c)(1), (2), (4) Date: Nov. 22, 2004

(87) PCT Pub. No.: WO03/074075

PCT Pub. Date: Sep. 12, 2003

(65) Prior Publication Data

US 2005/0075288 A1 Apr. 7, 2005
US 2005/0239698 A2 Oct. 27, 2005

(30) Foreign Application Priority Data

Mar. 5, 2002 (IT) .................... RM2002A000119

(51) Int. Cl.
*A61K 8/64* (2006.01)
*A61K 8/02* (2006.01)
*A61K 38/00* (2006.01)

(52) U.S. Cl. ................ 424/70.14; 424/78.02; 424/78.03; 424/401; 514/2

(58) Field of Classification Search ................ 530/350; 514/12; 435/6, 69.1; 424/70.14, 78.02–78.03, 424/401
See application file for complete search history.

(56) References Cited

U.S. PATENT DOCUMENTS 5,919,899 A 7/1999 Persico et al.

FOREIGN PATENT DOCUMENTS

WO WO 200156593 A2 * 8/2001

OTHER PUBLICATIONS

Ziche, M.Z., et al. 1997 Laboratory Investigation 76(4): 517-531.*
Failla, C.M., et al. 2000 J. Invest. Derm. 115(3): 388-395.*
Maglione, D., et al. 1991 PNAS 88: 9267-9271.*
Bed Sores reference sheet (University of Maryland) 2 pages.*
Sunburn reference sheet (University of Maryland) 2 pages.*
Ulcus Cruris reference sheet (www.dermis.net) 2 pages.*

* cited by examiner

*Primary Examiner*—Karen Cochrane Carlson
*Assistant Examiner*—Marsha Tsay
(74) *Attorney, Agent, or Firm*—Joseph Fischer; Beusse Wolter Sanks Mora & Maire, P.A.

(57) ABSTRACT

The invention relates to the preparation of placental growth factor (PLGF)-comprising therapeutic and cosmetic compositions capable of increasing angiogenesis of the cutaneous, subcutaneous and internal organ connective tissue. Such compositions are suitable for the treatment of pathological or natural states benefiting from the formation or regeneration of new vessels of the cutaneous compartment, such as scleroderma, its various manifestations, skin aging or loss of hair.

12 Claims, No Drawings

PHARMACEUTICAL AND COSMETIC COMPOSITIONS COMPRISING PLGF-1

CROSS-REFERENCE TO RELATED APPLICATIONS

This application is a National Stage entry under 35 USC 371 of International Application No. PCT/IT03/00132, filed Mar. 5, 2003, which claims priority to Italian Application No. RM2002000119, filed Mar. 5, 2002.

DESCRIPTION

1. Field of the Invention

The present invention relates to the preparation of therapeutic and cosmetic compositions capable of increasing angiogenesis of the cutaneous, subcutaneous and internal organ connective tissue, comprising the Placental Growth Factor (PLGF). Such compositions are therefore suitable for the treatment of pathological or natural states benefiting from the formation or regeneration of new vessels of the cutaneous compartment such as scleroderma, in its various manifestations, skin aging or loss of hair.

2. State of the Art

The placental growth factor (PLGF) is an angiogenesis-regulating homodimeric glycoprotein. The complete polynucleotide sequence encoding the PLGF protein was described by Maglione and Persico in Pat. EP-B-0 550 519 (WO-A-92/06194). Alternative splicings of PGLF RNA generate three homologous forms, specifically PLGF-1, PGLF-2 and PLGF-3, having polypeptide sequences that are different and all described in literature.

Therapeutical applications of PLGF-1 are described or merely hypothesized in the state of the art. Patent EP-B-0550519 hypothesizes the use of PLGF in the treatment of generic inflammatory states, wounds, burns, ulcers and postoperative stages. International Appln. WO-A-01/56593 describes the parenteral systemic use of the VEGF and PLGF factors in the treatment and in the prevention of cerebral, myocardial and peripheral ischemia. The scientific article published on the "Il Farmaco", Vol. 55, (2000), pages 165-167 (Maglione et al.) describes as well the PLGF-1 effect of prevention of myocardial ischemia and of reduction of infarct severity. Lastly, Faille et al. in "Journal Invest. Dermatol.", 115(3), September 2000, pages 388-395, report that PLGF production is induced in keratocytes involved in wounded tissue repair processes. However, the prior technical teaching does not allow to conclude that PLGF-1 be effective in the preventive or curative treatment of diseases or of pathological alterations involving the cutaneous, subcutaneous and internal organ connective tissue. In particular, prior art teachings do not allow to conclude that the local administration of exogenous PLGF be capable of influencing in vivo the cutaneous vascularisation with regard to pathological states, as well as to natural situations. An effect of promoting angiogenesis, and in particular of promoting cutaneous vascularisation, following exogenous PLGF administration as obtained in accordance with the present invention, is particularly advantageous in the treatment of pathological or physiological states susceptible of improvement due to a more effective blood supply.

SUMMARY OF THE INVENTION

The invention is based on the unexpected finding that an increase in PLGF-1 levels in the tissues constituting the cutis, and in particular in the connective tissue, is accompanied by an increase in the cutaneous vascularisation. Likewise, it has been observed that said increase in tissutal PLGF-1 levels may be advantageously achieved through the administration of exogenous PLGF-1 using the parenteral or topic compositions in accordance with the present invention. Angiogenesis stimulation proved useful in the treatment of pathologies typical of the cutaneous, subcutaneous and internal organ connective tissue, such as scleroderma, in its different manifestations of localized scleroderma, progressive systemic scleroderma and systemic sclerosis, in repairing cutaneous lesions and ulcers, natural or pathological baldness, or merely physiological situations such as skin aging, specifically due to solar exposure or to atmospheric/environmental aggressive agents.

Object of the present application is the use of PLGF, in particular of type 1 PLGF (PLGF-1), for the preparation of therapeutic or cosmetic compositions promoting angiogenesis in the preventive or curative treatment of diseases or of natural or pathological alterations involving the cutaneous, subcutaneous and internal organ connective tissue and/or the vascular system.

Specifically, object of the present invention is the use of PLGF-1, for the preparation of therapeutic compositions for the treatment of scleroderma, in particular of localized scleroderma, of progressive systemic scleroderma, of systemic sclerosis, of pathological skin aging due to exposition to atmospheric/environmental aggressors or to solar irradiation, and of baldness of pathological origin.

A further object of the invention is the use of PLGF-1 in the cosmetic preventive and curative treatment of hair loss and of skin aging.

Further object of the invention are also pharmaceutical compositions for topical and parenteral use, as well as cosmetic compositions for local use comprising PLGF-1 and excipients usual in the field of pharmaceutical and cosmetic compositions.

DETAILED DESCRIPTION OF THE INVENTION

The increase in PLGF-1 levels in the tissues constituting the skin, and in particular in keratinocytes, is accomplished by a local increase of vascularisation. Such an increase in PLGF-1 levels in tissues may be achieved by systemic as well as by local administration of exogenous PLGF-1.

Assays

The angiogenic action of PLGF-1 was determined by known methods conducted in vivo or in vitro, such as the rabbit cornea vascularisation assay or the chick chorionallantoic membrane vascularisation assay. In accordance with the present invention, cutaneous vascularisation was examined via computerized morphometric analysis of skin samples as described by Streit et al. (Proc. Natl. Acad. Sci. USA 1999, Dec. 21$^{st}$, 96(26), 14888-14893). Skin sections isolated from laboratory animals, treated or untreated according to the present invention, were immuno-histochemically stained employing monoclonal antibodies anti-CD31 or the used animal. The sections thus treated were analyzed by electron microscopy, and the morphometric analysis of the tissues was conducted using the IP-LAB program (Scanalytics, Inc.). The number of blood vessels per mm2, their average sizes and the related area occupied by them were determined as described by Streit et al.

In treated animals, local treatment with exogenous PLGF-1 caused a significant increase in the vascular parameters considered as illustrated in the examples.

A second method employed to estimate the angiogenic activity of the compositions according to the invention is the microscopic capillaroscopy and capillarometry in vivo. This known technology envisages the direct microscopic observation of the cutis, preferably pretreated with transparence-enhancing substances, like vaseline or vegetable oils. The preferred analysis zone is the limb finger nail wall. Analysis of data obtained by capillaroscopy and capillarometry can suitably be carried out by employing photographic recording systems and computerized data reprocessing systems. The parameters considered are the vascular morphology, the perivascular tissue morphology and the rheological aspect. The morphological observation records any vascularisation increase or diminution, capillary lumen and capillary density per $mm^2$. The tissue observation assesses the connective tissue transparency, the presence of hemorrhage or of lipid or sclerosed collagen deposits around the capillary vessels. In particular, the observation of the perivascular connective tissue highlights, under normal conditions, the capillary loop surrounded by a lighter-colored halo, denominated capillary halo, made of glucosaminoglycanes-rich lax tissue. The disappearance or reduction of such halo is a sign of a deep structural alteration of the connective tissue. Other alteration types are the reduced tissue transparency accompanying scleroderma. The rheological aspect assesses the flow rate or the presence of erythrocyte aggregates or of thrombosis.

The activity of the compositions of the invention in the treatment of scleroderma was assessed on animal model as described by Yamamoto T. et al. in Arch. Dermatol. Res. November 2000, 292(11), pages 535-541. A sclerodermal state is induced in C3H mice through a treatment with bleomycin (100 mcg/ml) subcutaneously injected daily for 3 weeks. After 3 weeks, the animals are sacrificed and skin samples of the treated zones are subjected to histologic analysis. The effect of the treatment points out histological manifestations attributable to the bleomycin-induced cutaneous sclerotization, and in particular cutaneous thickening and high hydroxyprolin levels.

PLGF

The type 1 Placental Growth Factor (PLGF-1) employed in the present invention may be of extractive origin, or obtained as an expression product from genetically modified host cells. In the preferred embodiment of the invention, a highly purified factor is employed in an essentially homodimeric or multimeric form obtained in accordance with the method disclosed by the present inventors in the International application PCT/IT 02/00065. In particular, a product comprising no less than the 98.5% of dimeric and multimeric active forms, no less than the 70% of dimeric form and anyhow no more than the 1.5% of monomeric form is used. Functionally active PLGF-1 fragments may likewise be used within the scope of the invention. Fragments exhibiting at least the 30% of the specific activity of the purified factor, or preferably at least the 50% or better at least the 90% of the same activity may be considered as functionally equivalent to the natural factor.

Diseases

Scleroderma treatment is one aspect of the invention, respectively of the compositions of the invention.

Scleroderma is a disease involving the microvascular system and the cutaneous, subcutaneous and internal organ connective tissue. The disease induces fibroblast activation and an excessive production and tissural and perivascular deposit of collagen, heavily contributing to the formation of fibrosis and of calcification zones, and therefore to the manifestation of the disease-induced symptoms. In particular, under capillaroscopy it is observed that vast amounts of sclerosed collagen surround the cutaneous vessels, causing vascular lumen narrowing.

There are differentiated a localized scleroderma with cutaneous involvement, characterized by skin hardening and thickening due to excessive and inadequate collagen deposition, and a progressive systemic scleroderma, in which, blood vessel involvement and systemic sclerosis with visceral lesions associate to the cutaneous fibrosis. The cutis, above all that of fingers and hands, appears hardened, thickened and edematous. Moreover, the disease manifests itself at myocardial level with cardiac insufficiency, at pulmonary, gastrointestinal, renal and osteo-muscular system level. Moreover, some patients develop cutaneous fibrosis-induced erosive arthropaties that enormously complicate the movability of the joints.

It has been reported, with regard to other angiogenic drugs, that angiogenesis promotion, in particular cutaneous angiogenesis promotion, due to the treatment with said drugs, is beneficial to the case history of the disease. In particular, in vivo capillaroscopy analysis of skin surfaces of patients affected by systemic sclerosis treated with angiogenic factors demonstrated a statistically significant vascularization increase, in density as well as in mean vessel calibre. Moreover, the new vessels are free from sclerosed collagen and therefore capable of improving blood supply to the tissue. This increase is accompanied by a partial remission of the pathological manifestations.

Without wishing to bind or limit the invention to scientific theories, it is hypothesized that the therapeutic effect exerted by PLGF-1 on animal model, in the treatment of systemic sclerosis, is mediated by the vasodilating action accompanying angiogenesis in vivo. In fact, it has been demonstrated that one of the effects induced by PLGF-1 is that of stimulating the generation of Nitrogen oxide (NO), indicated by many scientific evidences as an important vasodilation mediator.

The action mechanism presumably at the basis of the effect produced by PLGF-1 in the treatment of scleroderma and of its collateral manifestations, appears in accordance with the therapeutic treatment of these pathologies so far. In fact, this treatment relies on the combined use of different medicaments, among which agents having a vascular and mainly vasodilatory action.

A second aspect of the invention relates to the treatment of the phenomena typical of skin aging. Such a treatment, though deemed to be essentially cosmetic, entails therapeutic implications when taking into account cutaneous tissue early deterioration phenomena, due to protracted exposure to solar irradiation (photo-aging), to other radiations or to other environmental/atmospheric aggressors.

Electron microscopy on photo-damaged skin samples reveals a typical microvascular morphology, characterized, among other manifestations, by the presence of pathologically dilated capillars, elastin-lined or surrounded by a dense amorphous material. A presence of activated endothelial cells bearing an increased number of cytoplasmic organelles and of pinocytotic veshicles is also observed. It has been observed that the stimulation of a new cutaneous vascularization caused by the administration of PLGF-1, in accordance with the invention, generates in naturally as well as precociously aged skin a modulation effect onto the extracellular matrix responsible for the skin tone and thickness. The increased capillary vascularization following protracted local treatment with the compositions of the invention is accompanied by fibroblast increase and by production of new collagen, followed by a general improvement of the skin appearance.

Another aspect of the invention concerns the loss of hair.

The improved cutaneous vascularization is accompanied by a further manifestation of therapeutic as well as of cosmetic importance, i.e. the modulation of the growth of cutaneous annexes (hair, etc.) intended as loss prevention and regeneration promotion.

The anagen phase, corresponding to the hair growth phase, is accomplished by a natural increase of capillary follicle vascularization. The angiogenic action of locally applied PLGF-1 promotes such a vascular increase and the consequent hair growth. Computerized morphometric analysis of skin sections near the hair follicle of animals treated with the compositions of the invention revealed not merely an increase in capillary lumen size and in capillary density, and hence a general increase in the perifollicolar vascularization, but also an increase in the hair bulb dimensions and in the hair diameter itself.

The effect of preventing the loss of hair or of promoting its regrowth finds application not only in the case of natural loss, but also in the case of loss due to clinically relevant states like alopecia, hormonal disorders, chemotherapy, radiotherapy or medicament administration.

Any formulation suitable for the systemic or local administration of therapeutic agents may be used in accordance with the invention. Formulations for local use are used in the field of cosmetic applications.

In particular, the PLGF-1 factor may be administered by parenteral route with a systemic or local effect, or by topic route on skin or mucosae, with a mainly local effect. A systemic effect is mainly achieved by endovenous administration, though intraperitoneal or intramuscular administration are suitable as well. A local effect is achieved via topic, or parenteral intramuscular, subcutaneous, intraarticular administration. Likewise, the PLGF-1 factor may be locally administered via electrotransport or ionophoresis. Subcutaneous implants are likewise useful when a delayed release is desirable. The oral administration of the factor, though it also viable, is less advisable in view of the active product perishability.

Compositions for parenteral, systemic or local use comprise solutions, suspensions, liposome suspensions, W/O or O/W emulsions. Compositions for topical use comprise solutions, lotions, suspensions, liposome suspensions, W/O or O/W emulsions, gels, ointments, creams, pomades and pastes. In a preferred embodiment the active substance is formulated in a lyophilised form, mixed to suitable lyophilization additives and ready to be redissolved with therapeutically acceptable diluents. Useful lyophilization additives are buffers, polysaccharides, suchrose, mannitol, inositol, polypeptides, amino acids and any other additive compatible with the active substance. In a preferred embodiment of the invention the active substance is dissolved in phosphate buffer ($NaH_2PO_4/H_2O$—$Na_2HPO_4/2H_2O$) in an amount such that the post-lyophilisation PLGF1/phosphate ratio is comprised between 1:1 and 1:2. Diluents suitable for parenteral use are: water, physiological solutions, sugar solutions, hydroalcoholic solutions, oily diluents, polyols, like glycerol, ethylene or polypropylene glycol, or any other diluent compatible with the administration method as for sterility, pH, ionic strength and viscosity.

In the case of emulsions or suspensions, the composition may contain suitable surfactants of non-ionic, zwitterionic, anionic or cathionic type commonly used in the formulation of medicaments. Oil/water (O/W) hydrophilic emulsions are preferable for parenteral systemic use, whereas water/oil (W/O) lipophilic emulsions are preferable for local or topic use.

Moreover, the compositions of the invention may contain optional additives like isotonic agents, such as sugars or polyalcohols, buffers, chelating agents, antioxidants, antibacterials.

The compositions for topic use comprise liquid forms or semisolid forms. The liquid forms comprise solutions or lotions. These may be aqueous, hydroalcoholic, like ethanol/water, or alcoholic and are obtained by solubilizing the lyophilized substance.

Alternatively, active substance solutions may be formulated in form of gel by addition of known gelling agents, like: starch, glycerin, polyethylene or polypropylene glycol, poly(meth) acrylate, isopropyl alcohol, hydroxystearate.

Other types of compositions for topic use are emulsions or suspensions in form of pomades, pastes, creams. W/O emulsions are preferable, providing a faster absorption. Examples of lipophilic excipients are: liquid paraffin, anhydrous lanolin, white vaseline, cetyl alcohol, stearyl alcohol, vegetable oils, mineral oils. Agents increasing cutaneous permeability, thereby facilitating the absorption, may advantageously be used. Examples of such agents are physiologically acceptable additives like polyvinyl alcohol, polyethylenglycol or dimethylsulfoxide (DMSO).

Other additives used in the topic compositions are isotonic agents, like sugars or polyalcohols, buffers, chelating agents, antioxidants, antibacterials, thickeners, dipersants.

Likewise, delayed-release compositions for local or systemic use may be useful, and comprise polymers like polylactate, poly(meth)acrylate, polyvinylpyrrolidone, methylcellulose carboxymethylcellulose and other substances known in the art. Delayed-release compositions in form of subcutaneous implants based on, e.g., polylactate or other biodegradable polymers may be useful as well.

Though the active substance is preferably packaged in lyophilized and hence stable form, the pharmaceutical compositions advantageously comprise substances stabilizing the PLGF-1 in the active dimeric-multimeric forms. Such stabilizers inhibit the formation of intermolecular disulfide bonds, thereby preventing the polymerisation of the active substance. However, the amount of stabiliser should be carefully measured in order to concomitantly prevent the reduction of the active substance to the inactive monomeric form. Examples of such substances are: Cystein, Cysteamine, or glutathione in reduced form.

Dosage

The dosage depends on the administration route and on the formulation selected. For parenteral administrations, amounts range from 1 mcg/Kg/day to 500 mcg/Kg/day, preferably from 10 mcg/Kg/day to 200 mcg/Kg/day. Such administrations are obtained with pharmaceutical compositions comprising about from 50 mcg to 30 mg per unitary dose, preferably about from 500 mcg to 10 mg per dose. For topical therapeutic application, the amounts ranging from 0.1 to 10 mg per gram of composition proved to be effective. Local cosmetic compositions for the treatment of skin aging or loss of hair preferably comprise from 0.01 to 0.09 mg of active substance per gram of composition.

The length of treatment varies depending on the pathology or on the desired effect. In the case of scleroderma treatment the application ranges from 1 day to 12 months according to the pathology severity. In the case of a treatment against natural or early aging of the skin, the application ranges from 1 to 400 days, preferably for at least 30 days. Likewise, in the case of a treatment for preventing loss of hair or for promoting hair regrowth the application ranges from 1 to 400 days.

EXAMPLE 1

Solution for Parenteral Use 58 milligrams of lyophilized substance, comprising 25 mg of pure PLGF-1 and 33 mg of phosphate buffer (10 mg $NaH_2PO_4/H_2O$ and 23 mg $Na_2HPO_4/2H_2O$), and about 125 ml physiological solution for parenteral use, are separately packaged in flasks preset for mixing the lyophilized product with the diluent immediately prior to use. The post-solubilisation concentration of active substance is of about 0.2 mg/ml.

EXAMPLE 2

W/O Emulsion for Topic Application

An amount of lyophilized substance comprising 20 mg active substance is brought to 5 ml 10% ethanol hydro-alcoholic solution comprising 10% DMSO. The solution is emulsified in sterilized vegetable oil for cutaneous application using a surfactant suitable for W/O emulsions having a <10 HLB coefficient. The emulsion contains active substance equal to about 2 mg/gr of composition.

EXAMPLE 3

O/W Emulsion

An amount of lyophilized substance comprising about 20 mg active substance is solubilized in 5 ml of hydro-alcoholic solution comprising 30% DMSO and emulsified with a suitable surfactant in a vegetable oil-based lipophilic solvent. The resulting O/W emulsion contains the active substance at a concentration of about 3 mg/gr composition.

EXAMPLE 4

Topical Composition in Form of Gel

An amount of lyophilized substance comprising 10 mg of active substance is brought in 20 ml 10% ethanol hydro-alcoholic solution comprising 20% DMSO. Then, the solution is additioned with a mixture of polyethylene glycol (400-4000) and polypropylene glycol. The active substance is present in an amount equal to 0.2 mg/gr composition. The gel is suitable for cosmetic application.

EXAMPLE 5

4 SKH-1 hairless mice were treated daily for 20 days with 50 microliters of the solution described in Example 1 (0.2 mg/ml) via a parenteral subcutaneous route on a set skin surface (1 $cm^2$) on the dorsal area. Other 4 SKH-1 mice were treated for 30 days with the composition described in Example 2 (2 mg/gr) via a topic route. 4 mice of the same kind were treated with the sole excipients for parenteral use and other 4 with the sole excipients for topic use, adhering to the same administration regimens. Skin samples of the sacrificed animals were examined through computerized morphometric analysis as described by Streit et al. (supra).

In detail, skin sections (5 micron) were immuno-histochemically stained using monoclonal anti-mouse CD31 antibodies. The sections thus treated were analysed by electron microscopy, and the morphometric analysis of the tissues was effected using the IP-LAB program (Scanalytics Inc.) The parameters considered were the vessel-covered area (% per mm2) and the average vessel size ($\mu$m2). The results are reported in Table 1.

TABLE 1

| Parameter | Parenteral Placebo | Topical Placebo | Parenteral PLGF-1 | Topical PLGF-1 |
|---|---|---|---|---|
| Vessel area (mm2) (%) | 4.3 ± 0.2% | 4.1 ± 0.2% | 6.2 ± 0.3% | 5.2 ± 0.6% |
| Vessel size ($\mu$m2) | 180 ± 9 | 176 ± 9 | 279 ± 14 | 235 ± 12.7 |

The values reported in the Table exhibit statistically significant increases, both with regard to the parenteral treatment and to the topical treatment, though the increase is less marked for the topical treatment.

EXAMPLE 6

In this example the animal model of bleomycin-induced scleroderma described by Yamamoto et al. (supra) was used.

A first group of C3H mice was treated with bleomycin (100 mcg/ml) subcutaneously injected daily for 3 weeks. Other 3 groups of C3H mice were treated like the first group, yet to their daily injection PLGF-1 was added, at 0.1, 1 and 10 mcg/ml, respectively. After 3 weeks of treatment the animals were sacrificed, and the skin of the treated zones was collected and subjected to histological analysis. The effect of the treatment with PLGF-1 at 1 and 10 mcg/ml, yet not at 0.1 mcg/ml, highlighted a significant reduction in the histological manifestations attributable to bleomycin-induced cutaneous sclerotization. In particular, the cutaneous thickening and the hydroxyproline levels are significantly decreased with respect to the mice treated with the sole bleomycin.

EXAMPLE 7

The back of the left hand of healthy adult individuals of age ranging from 50 to 60 years, usually markedly exposed to environmental aggressors and to solar irradiation, was treated with cutaneous topic applications of the composition in form of gel described in example 4. The amount applied was of 1 gr gel, corresponding to 0.2 mg active substance per day, for 60 days in summertime. The effect of the treatment was assessed with capillaroscopic and capillarometric analysis, with storing and computerized reprocessing of the observed data. Analysis of the non-treated surfaces highlighted the typical picture of cutaneous early photo-aging, characterised by the presence of pathologically dilated capillaries, elastin-lined or surrounded by dense amorphous material.

At a macroscopic level, the treatment yielded to general improvement of skin tone and appearance.

In particular, capillaroscopy analysis highlighted the capillary vascularization increase to be particularly apparent in the hair perifollicolar areas. The comparison, conducted by capillarometry, of the perifollicolar area of surfaces treated or not treated with the composition at issue highlighted an increase of about the 35.0% in the number of vessels per mm2. It being known that an increase in the vascularisation of the hair follicle stimulates its growth, the hereto-reported data prove that the topic treatment with PLGF-1 is not merely effective against skin ageing, but promotes capillary/hair growth as well.

What is claimed is:

1. A method of treatment of a state comprising preparing an angiogenesis promoting medicament comprising type 1 Placental Growth Factor (PLGF-1) as an active principle, and administering to an individual in need of said medicament to treat the state, wherein the state is selected from the group consisting of:
   scleroderma, and
   early skin aging due to exposures to atmospheric aggressive agents or to protracted solar irradiation and wherein the PLGF-1 is comprised in the medicament in an amount suitable for an administration of 1 to 500 μg per Kg of body per day.

2. The method according to claim 1, wherein the state is selected from the group consisting of localized scleroderma and progressive systemic scleroderma.

3. The method according to claim 2, wherein the localized scleroderma is cutaneous scleroderma and the progressive systemic scleroderma is myocardial scleroderma.

4. The method according to claim 1, wherein the medicament is in a form suitable for generating a local or systemic effect.

5. The method according to claim 1, wherein the medicament is in a form suitable for endovenous, intramuscular, intra-articular, subcutaneous or topical administration or subcutaneous implant or ionophoresis.

6. The method according to claim 1, wherein PLGF-1 is comprised in an amount suitable for an administration of 10 μg/Kg/day to 200 μg/Kg/day.

7. A method of cosmetic treatment of a state comprising administering to adult individuals type 1 Placental Growth Factor (PLGF-1) to promote cutaneous or subcutaneous angiogenesis, wherein the state is natural skin aging.

8. The method according to claim 7, wherein the PLGF-1 is formulated in a cosmetic composition for topical administration.

9. The method according to claim 7, wherein PLGF-1 is comprised in an amount suitable for an administration of 1 to 500 μg per Kg of body per day.

10. A method of treatment of a state comprising administering to adult individuals type 1 Placental Growth Factor (PLGF-1) to promote perifollicolar angiogenesis, wherein the state is loss of hair.

11. The method according to claim 10, wherein the medicament is in a form suitable for endovenous, intramuscular, intra-articular, subcutaneous or topical administration or subcutaneous implant or ionophoresis.

12. The method according to claim 10, wherein PLGF-1 is comprised in an amount suitable for an administration of 1 to 500 μg per Kg of body per day.

* * * * *